United States
Fonrojet et al.

[11] 4,146,295
[45] Mar. 27, 1979

[54] HOLOGRAPHIC DEVICE FOR OBTAINING A CODED IMAGE OF AN OBJECT EMITTING X-RAYS OR GAMMA-RAYS

[75] Inventors: Jacques Fonrojet, Paris; Yves Belvaux, Versailles; Serge Lowenthal, Paris, all of France

[73] Assignee: Agence Nationale de Valorisation de la Recherche (ANVAR), Neuilly-sur-Seine, France

[21] Appl. No.: 750,891

[22] Filed: Dec. 15, 1976

[30] Foreign Application Priority Data

Dec. 19, 1975 [FR] France ................ 75 39004

[51] Int. Cl.² .................... G03H 1/08; G03B 41/16
[52] U.S. Cl. .................... 350/3.66; 250/321; 250/363 S; 350/162 ZP
[58] Field of Search ............. 350/3.5, 162 R, 162 ZP, 350/3.66; 250/320, 321, 363 S, 368, 445 T

[56] References Cited

U.S. PATENT DOCUMENTS

| 3,829,688 | 8/1974 | Barrett | 350/162 ZP |
| 3,961,191 | 6/1976 | Stoner et al. | 250/368 |

OTHER PUBLICATIONS

Barrett et al., *Optical Engineering*, vol. 13, No. 6, Dec. 1974, pp. 539-549.
Miles, *Applied Optics*, vol. 7, No. 5, May 1968, pp. 976-977.
Barrett et al., *Optical Engineering*, vol. 12, No. 1, Feb. 1973, pp. 8-12.
Singleton et al., *IEEE Transactions on Biomedical Engineering*, vol. BME-23, No. 3, May 1976, pp. 239-246.

*Primary Examiner*—Ronald J. Stern
*Attorney, Agent, or Firm*—Weingarten, Maxham & Schurgin

[57] ABSTRACT

The invention provides a holographic device for X-ray or $\gamma$ ray imaging, especially for tomography in the medical field, in which low frequencies of radiation can be included in the image construction by virtue of having a mask with a particular transmittance law.

For example the transmittance law of the mask may be such that transmittance is a function of $x^2+y^2$ or of $\sqrt{x^2+y^2}$ where x and y are spatial co-ordinates of the mask.

2 Claims, 8 Drawing Figures

HOLOGRAPHIC DEVICE FOR OBTAINING A CODED IMAGE OF AN OBJECT EMITTING X-RAYS OR GAMMA-RAYS

FIELD OF THE INVENTION

The present invention relates to a device for carrying out so-called incoherent holography or a device for coding scintillographic or radiographic images with the aid of coding screens, or masks, for use in astronomical and medical gammagraphic applications.

The invention more particularly relates to a holographic device for obtaining a coded image of an object constituted by a set of radiation sources, especially X-ray or γ-ray sources, the device being of the type comprising mask means with predetermined spatial transmittance variation receiving the radiations from the object and detector means placed downstream from the mask means.

BACKGROUND OF THE INVENTION

The known devices of this type generally use a mask having a centric Fresnel configuration. Although perfectly suitable for the case of punctiform objects such as stars, these known devices give rise to numerous difficulties in the case of continuous objects such as human organs which have been marked with radioactive tracers. In particular, the centric Fresnel region leads to the superimposition of the various diffracted orders. In order to remedy these difficulties, it has already been proposed to use, as a coding screen or mask, an eccentric portion of a Fresnel configuration. However, such an incoherent holographic device behaves, from the point of view of imaging, as a pass-band filter cutting off the elements of low spatial frequency. It then becomes necessary to arrange, either on or in the vicinity of the object whose image is desired, a second mask which modulates the object to the mean frequency transmitted by the Fresnel region.

The invention eliminates these disadvantages and, in particular, it has as its object the provision of a device in which a single mask is used.

SUMMARY OF THE INVENTION

According to this invention the holographic device comprises mask means having a predetermined spatial transmittance variation and disposed to receive radiations from said sources constituting the object, and detector means placed downstream from the mask means, said mask having a configuration such that it is possible to avoid the superimposition of different diffraction orders without cutting off low frequency radiations from said object.

Advantageously, the mask means has two spatial variables, and a spatial transmittance variation which has a configuration substantially corresponding to a function which is the product of a code of said two spatial variables multiplied by a linear periodic function.

In a preferred form of the invention said mask means includes a planar synthesiser mask having a discrete spatial transmittance variation, and means for setting said synthesiser mask in motion in its plane.

Conveniently, the mask possesses continuous transmittance variation according to a spatial function of $\sqrt{x^2 + y^2}$ and it is synthesised by a synthesiser mask which displays a configuration with discrete transmittance variation and which is set in a rotary motion about its centre. Alternatively, the mask may have a continuous transmittance variation in accordance with a periodic spatial function of $x^2 + y^2$.

Suitably, the mask means and the detector means are set in translatory motions, in their plane, which are homothetic with respect to each other relative to a predetermined plane passing through the object.

The synthesiser mask desirably includes at least one figure in the shape of a sector and is mounted to rotate about the apex of the said sector.

DETAILED DESCRIPTION OF THE INVENTION

Other objects and advantages of the present invention will be better understood by reference to the following description and drawings relating to several exemplary embodiments. In the drawings.

By way of example, and to help in understanding, there will be described a device which is suitable for obtaining a gammagraphic image of a human organ marked with a radioactive tracer. It is self-evident that this description is not to be in any way limiting with regard to either the type of object of which gammagraphy or radiography is carried out or the type of receiver used. The receiver can instead be constituted by an X-ray film and intensifier screens or may comprise a scintillating crystal or a luminance amplifier or may be a wired receiver, for example.

Figure 1:
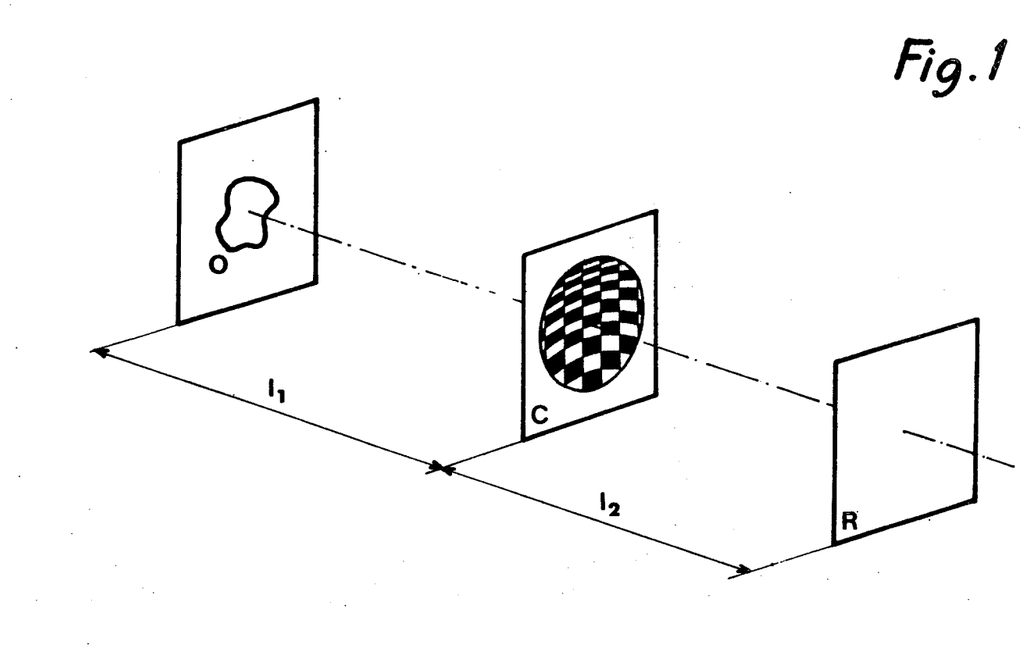
FIG. 1 is a schematic view of a holographic device according to one embodiment of the invention.

In a typical device, shown in FIG. 1, the organ O marked with a radioactive tracer is located at a distance $l_1$ from the mask C, which is in turn located at a distance $l_2$ from the photosensitive receiver R, the plane of which is parallel to that of the mask C. The distances $l_1$ and $l_2$ are of the order of a few centimeters to a few decimeters. The mask C used can be either of two types: namely the discrete type or the continuous synthetic type.

1. Discrete masks

In order to remedy the disadvantages already mentioned of the centric or eccentric Fresnel regions, the mask C in one embodiment of the invention displays a configuration which corresponds in a first approximation to a law of transparency of the form:

$$T = 1 + m \genfrac{}{}{0pt}{}{\sin}{\cos} \left\{ a(x^2 + y^2) + \gamma \right\} \cos bx.$$

where $\cos^{\sin}$ indicates that either the sine or cosine function may be selected, in the alternative.

This configuration thus results from the product of a spatial coding function with two spatial variables, such as that of a centric or eccentric Fresnel region, multiplied by a linear periodic function of the network, such as the function cos bx, of one spatial variable.

Figure 2A:
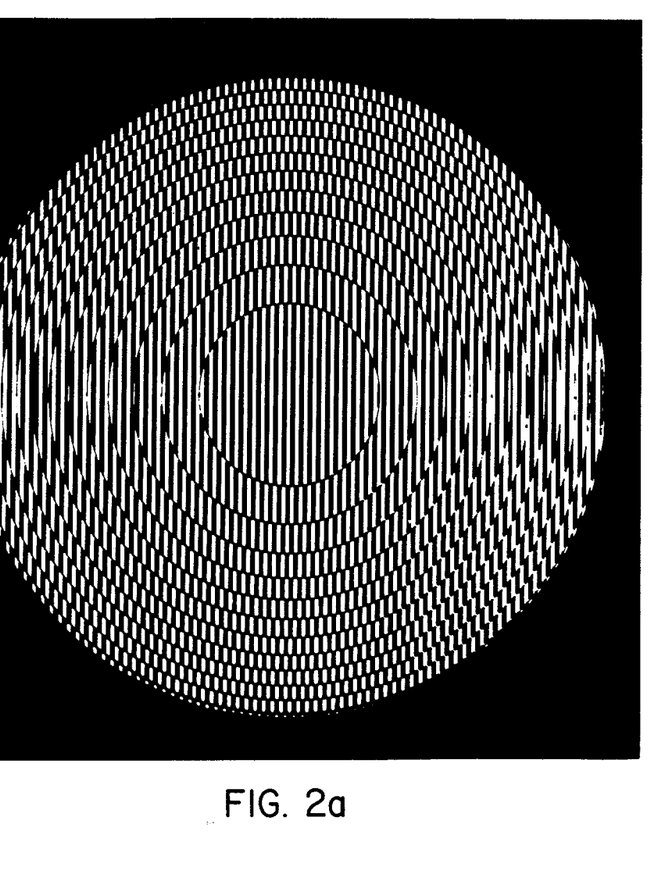
FIG. 2a is a mask according to one embodiment of the invention.
Figure 2B:
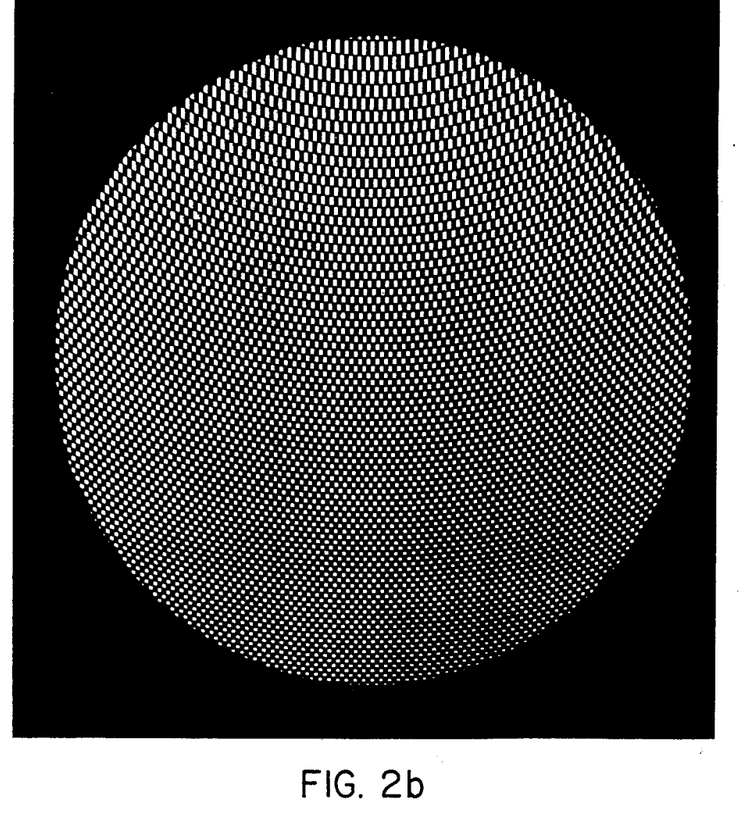
FIG. 2b is a mask according to another embodiment of the invention.

FIGS. 2a and 2b show the approximation of a mask of such a type, depending on whether the central portion (FIG. 2a) or an eccentric portion (FIG. 2b) of the Fresnel configuration is being considered.

2. Synthetic "half-tone" masks

It is very difficult to produce continuous (i.e. non-binary or discrete) modulating screens displaying a transmittance which follows a well-defined law.

In general, the screens used are of the discrete variation or binary type, that is to say they only display zones which are either totally opaque or totally transparent to the radiations emitted by the object. This, however, may lead to spurious images when they are used in gamma-holography.

Figures 3A, 3B:
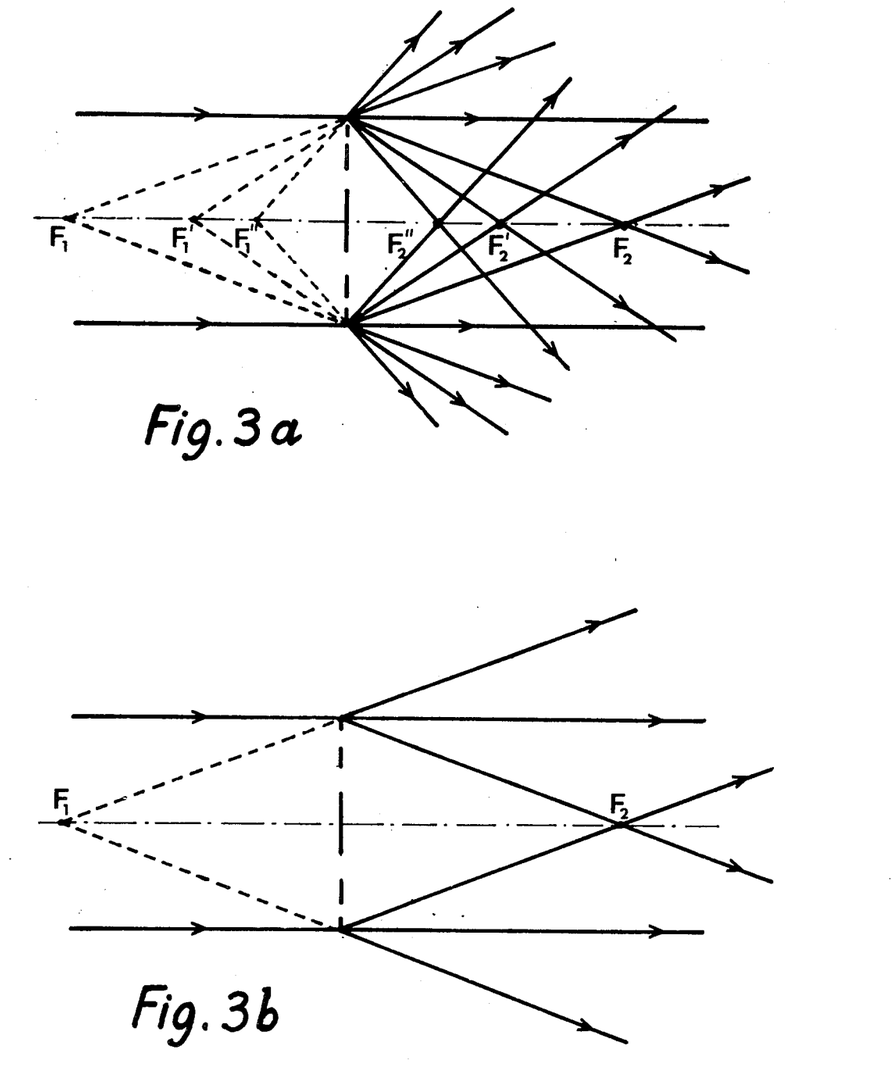
FIG. 3a is an optical diagram showing the trace of the light rays in the case where the mask employed is a binary Fresnel configuration.
FIG. 3b is an optical diagram showing the trace of the light rays in the case where the mask used is an exact Fresnel configuration.

Indeed, if the code used for the screen is manifested by alternatively opaque and transparent rings of the same surface, the Fresnel region thus constituted produces, during image reconstruction, a series of foci, that is to say images $F_2$, $F_2'$ and $F_2''$ as shown in FIG. 3a.

If it is possible to produce a screen whose transmittance configuration is that of an exact Fresnel region, the law of which is:

$$T = 1 + m \frac{\sin}{\cos}\left\{ a(x^2 + y^2) + \gamma \right\},$$

there remain only two diffracted orders $F_1$, $R_2$ (FIG. 3b).

Figure 4A:
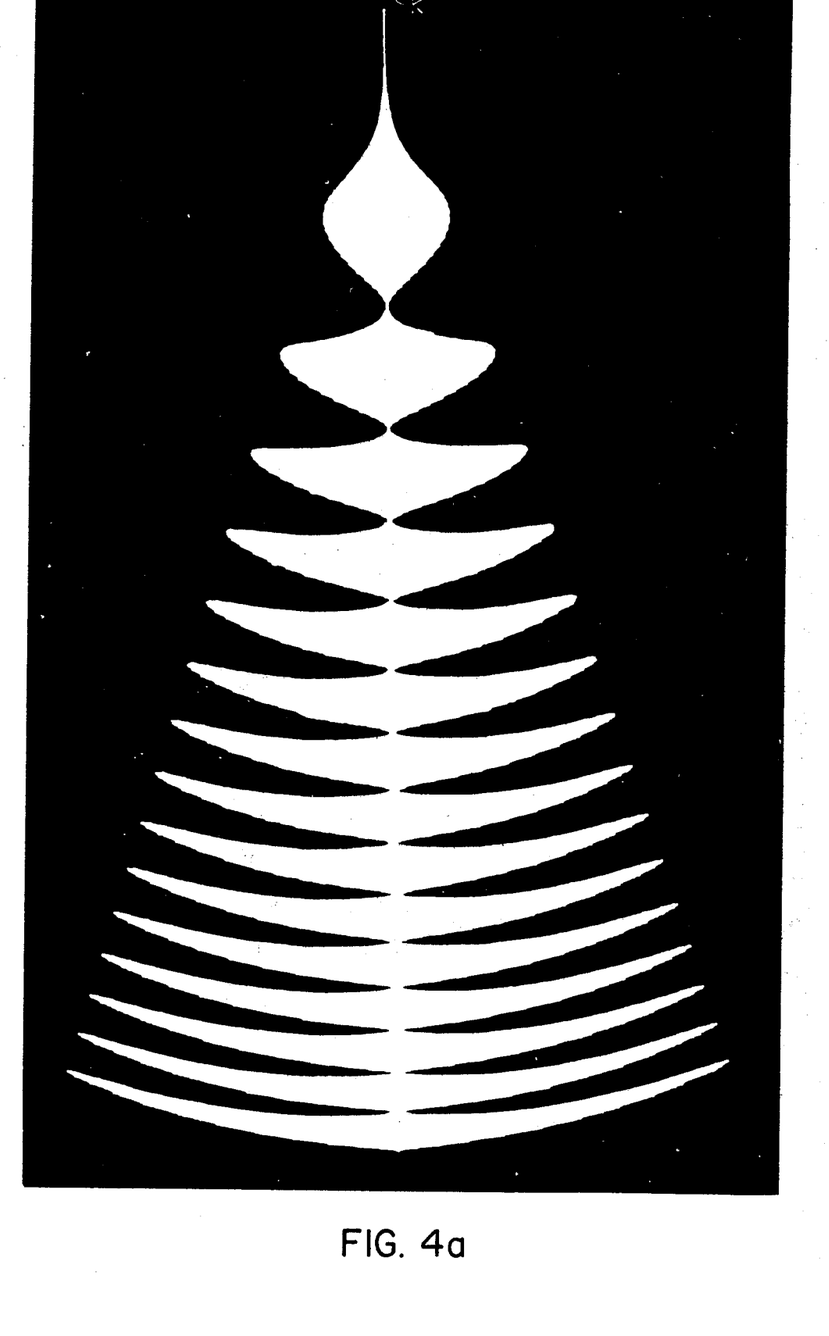
FIG. 4a is a binary synthesiser mask according to one embodiment of the invention.
Figure 4B:
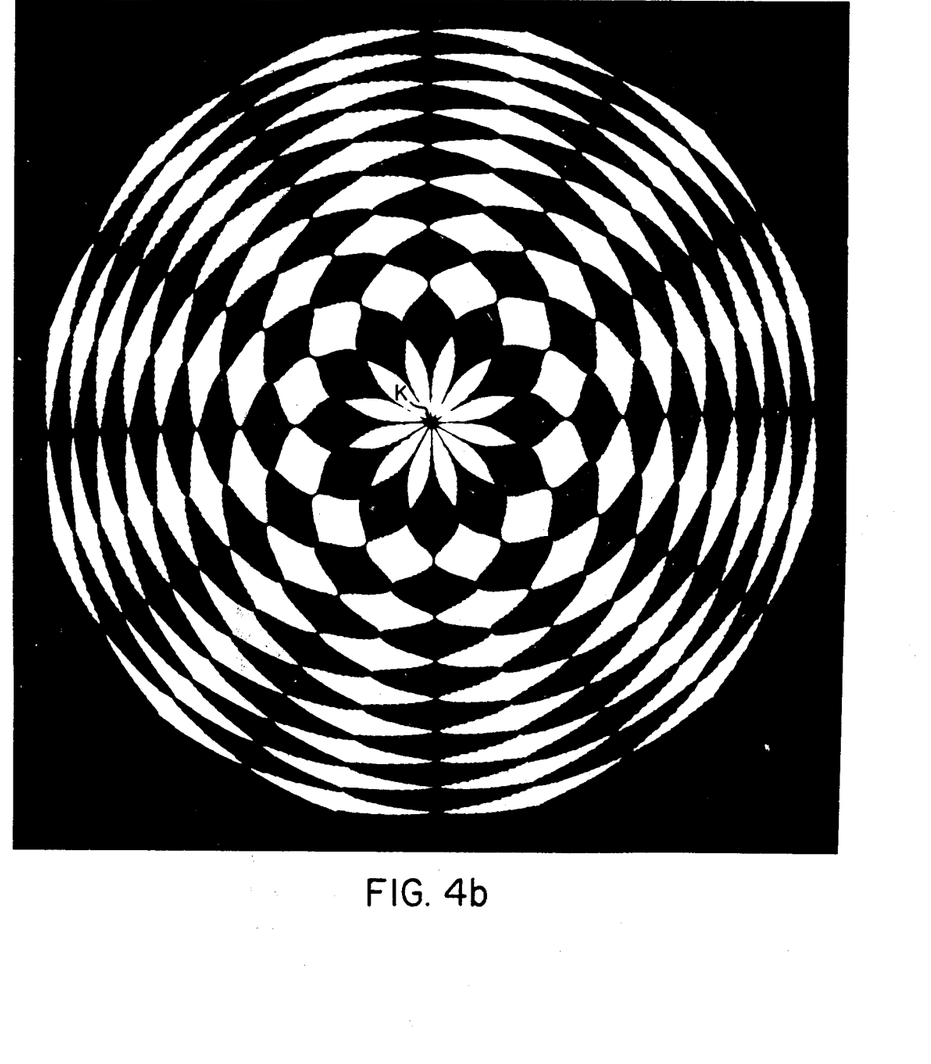
FIG. 4b is a binary synthesiser mask according to another embodiment of the invention.

In accordance with the invention such continuous configurations can be obtained from binary masks set in a predetermined motion. FIGS. 4a and 4b show two examples of a binary mask synthesising an exact Fresnel region when it is set in a rotary motion about its centre K and in its plane.

It will be noted that FIG. 4a shows only a part of a mask and that the complete mask will be formed of twelve sectors, each of which is identical to the portion of the mask illustrated in FIG. 4a. It is of course possible to produce a synthesiser mask comprising any number of sector-shaped portions such as are exemplified in FIG. 4b.

By using such binary masks set in translatory and/or rotary motion, it is possible to synthesise practically any desired continuous, or half-tone law of transparence.

With the masks of FIGS. 4a and 4b, or any mask of analogous configuration, it is possible to synthesise a spatial function in an exact Fresnel region. However, the invention is not limited to such functions, but on the contrary it extends to all continuous spatial functions of $\sqrt{x^2 + y^2}$, that is to say of the radius, be they periodic or not. These functions assume the existence of a centre, that is to say of the point of the coordinates $x = 0$, $y = 0$.

The binary synthesiser masks display, advantageously, at least one figure having the general shape of a sector, that is to say capable of being inscribed in a circular sector. As in the case of point K of FIG. 4a, the centre of the coding mask synthesised coincides with the apex of the said sector which is also the centre about which the binary mask must rotate to synthesise the said half-tone coding mask.

Figure 5:
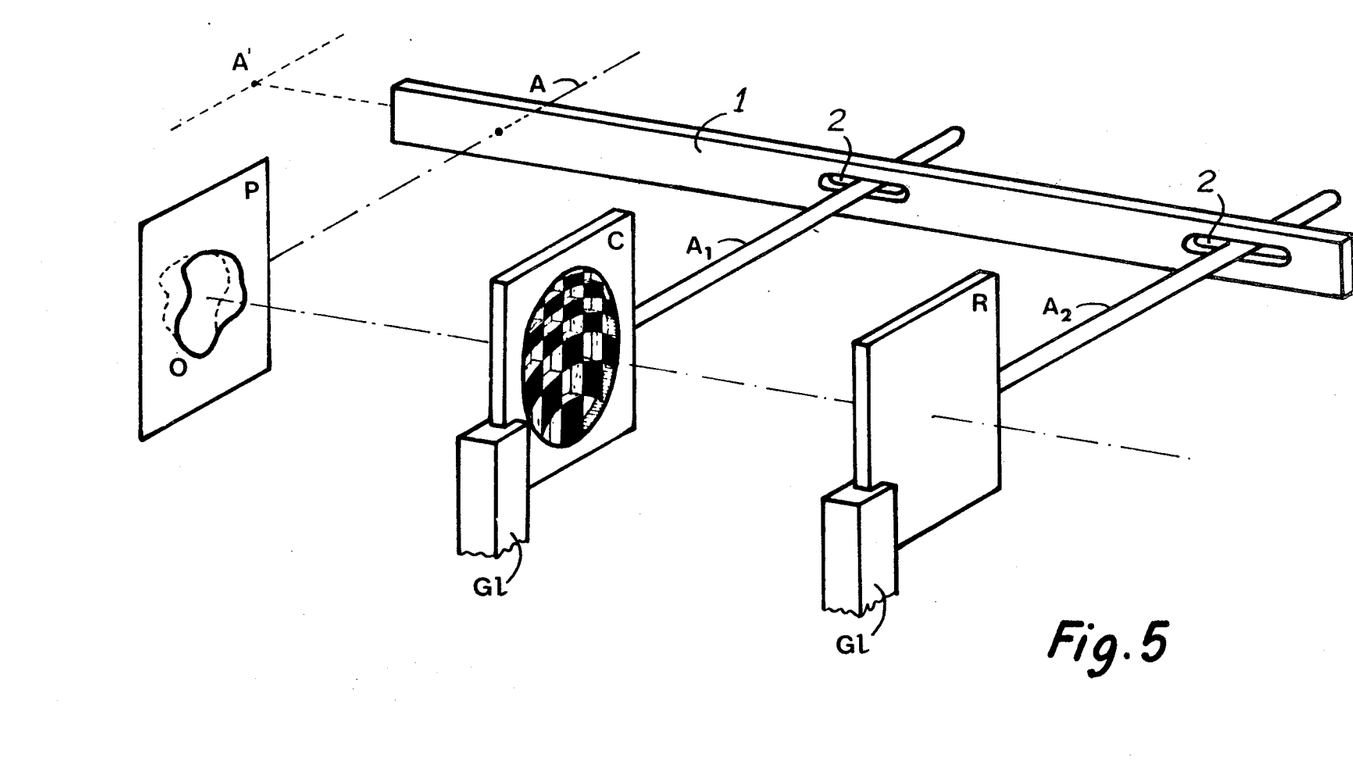
FIG. 5 is a schematic view of an embodiment of holographic device different from that of FIG. 1.

The coding masks described above can be used in a tomographic device such as the one illustrated schematically in FIG. 5.

The coding mask C and the receiver R are, in this case, each set in translatory movement within its plane, these translatory movements having velocities which are proportional to their distances from a plane P passing through the object O which has a given volume.

On FIG. 5, the functioning of the device has been illustrated schematically by a lever 1, articulated about an axis A in the plane P, where it is desired to effect a section of the object; the cam Ca possesses apertures 2 through which pass shafts $A_1$ and $A_2$ constituting the respective supports of the coding mask C and of the receiver R. In the embodiment shown in FIG. 5, slide guides G1 shown schematically in FIG. 5 maintain the said supports $A_1$, $A_2$ in their planes by limiting their motion to a vertical translation.

Given the relative velocities of the various elements C and R, everything can be considered, as regards the points of the object located in the plane P, as if the device were static, which makes it possible to obtain a coded image in the plane of the receiver R, as in the case of the device illustrated in FIG. 1. On the other hand, with regard to points of the object located outside the plane P, a scanning, that is to say a "shift" of the coded image occurs, and the device only sees those gamma-ray emitters which are located in the plane P. In this manner, a tomographic image of the object is produced.

It is self-evident that the device described above is given only for purposes of exemplification of the invention and does not in any way restrict the generality of the present invention. The axis A can be located in any one of the planes containing the three principal elements of the system: namely the tomographic plane P, the plane of the coding mask C, or the plane of the receiver R, the two other elements in each of these situations then being mobile relative to the fixed element O, C or R, respectively. The axis A can even be located outside any one of these three planes in which case all three elements O, R and L must then all be set in a translatory motion.

The lever 1, shown in FIG. 5 can, for example, rotate about an axis A', at a distance from the axis A. In this case the axis A, and thus the object O, will be set in a vertical translatory motion. However, it is simpler to leave the object (for example a patient) fixed and to arrange for translatory motion of the other elements C and R.

We claim:

1. A method for obtaining a coded image of an object constituted by a set of X-ray or γ-ray sources, comprising the steps of:

passing the radiation emitted from said sources through a binary plane mask having parts transparent for said radiation, whose pattern is designed by synthesizing an exact Fresnel zone plate by rotating about a point called center located in the plane of the mask, said mask being set in a rotary motion about its center and in its plane; and detecting said radiation downstream from said rotary mask, so as to avoid the superimposition of different diffraction orders in the detected coded image.

2. A holographic device for obtaining a coded image of an object constituted by a set of X-ray or γ-ray sources, such device comprising:

mask means comprising a binary plane mask having a center located in the plane of the mask and parts thereof being transparent for said radiation, whose pattern is designed for synthesizing an exact Fresnel zone plate by rotating about said center, said mask being set in rotary motion about its center and in its plane; and detector means placed downstream from the mask means.

* * * * *